United States Patent
Homma

(10) Patent No.: US 9,399,041 B2
(45) Date of Patent: Jul. 26, 2016

(54) FAT COMPOSITION

(71) Applicant: KAO CORPORATION, Chuo-ku (JP)

(72) Inventor: Rika Homma, Sunderland, MA (US)

(73) Assignee: KAO CORPORATION, Chuo-ku (JP)

( * ) Notice: Subject to any disclaimer, the term of this patent is extended or adjusted under 35 U.S.C. 154(b) by 0 days.

(21) Appl. No.: 14/350,955

(22) PCT Filed: Oct. 11, 2012

(86) PCT No.: PCT/JP2012/076305
§ 371 (c)(1),
(2) Date: Apr. 10, 2014

(87) PCT Pub. No.: WO2013/054841
PCT Pub. Date: Apr. 18, 2013

(65) Prior Publication Data
US 2014/0235596 A1   Aug. 21, 2014

(30) Foreign Application Priority Data

Oct. 12, 2011 (JP) ................. 2011-225235
Dec. 14, 2011 (JP) ................. 2011-273483

(51) Int. Cl.
| A01N 45/00 | (2006.01) |
| A61K 31/56 | (2006.01) |
| A61K 31/575 | (2006.01) |
| A23D 9/007 | (2006.01) |
| C11B 5/00 | (2006.01) |
| A23L 1/30 | (2006.01) |
| A61K 31/23 | (2006.01) |
| A23D 9/013 | (2006.01) |

(52) U.S. Cl.
CPC .............. *A61K 31/575* (2013.01); *A23D 9/007* (2013.01); *A23D 9/013* (2013.01); *A23L 1/3004* (2013.01); *A23L 1/3006* (2013.01); *A61K 31/23* (2013.01); *C11B 5/0014* (2013.01); *C11B 5/0021* (2013.01)

(58) Field of Classification Search
None
See application file for complete search history.

(56) References Cited

U.S. PATENT DOCUMENTS

| 5,998,396 | A | 12/1999 | Nakano et al. |
| 6,117,475 | A | 9/2000 | van Amerongen et al. |
| 6,492,538 | B1 * | 12/2002 | van Amerongen et al. ... 554/229 |
| 2002/0192318 | A1 | 12/2002 | Berry et al. |
| 2011/0177226 | A1 | 7/2011 | Nii et al. |
| 2012/0259133 | A1 | 10/2012 | Homma et al. |
| 2013/0023684 | A1 | 1/2013 | Moriwaki et al. |
| 2013/0230630 | A1 | 9/2013 | Homma et al. |
| 2013/0280407 | A1 | 10/2013 | Homma et al. |
| 2014/0170296 | A1 | 6/2014 | Homma et al. |

FOREIGN PATENT DOCUMENTS

| CN | 1399520 A | 2/2003 |
| CN | 1414834 A | 4/2003 |
| EP | 2 641 475 A1 | 9/2013 |
| EP | 2 656 737 A1 | 10/2013 |
| EP | 2 749 176 A1 | 7/2014 |
| EP | 2 749 177 A1 | 7/2014 |
| JP | 61-118318 A | 6/1986 |
| JP | 10-179086 A | 7/1998 |
| JP | 11-127779 A | 5/1999 |
| JP | 2001-224309 A | 8/2001 |
| JP | 2001224309 A * | 8/2001 |
| JP | 3597437 B2 | 9/2004 |
| JP | 2006-257064 A | 9/2006 |
| JP | 2011-115112 A | 6/2011 |
| WO | WO 01/32029 A2 | 5/2001 |
| WO | WO 01/32029 A3 | 5/2001 |
| WO | WO 01/37681 A1 | 5/2001 |

OTHER PUBLICATIONS

Extended European Search Report issued Jun. 1, 2015 in Patent Application No. 12839930.0.
U.S. Appl. No. 14/347,915, filed Mar. 27, 2014, Homma et al.
U.S. Appl. No. 14/347,888, filed Mar. 27, 2014, Homma et al.
U.S. Appl. No. 14/240,295, filed Feb. 21, 2014, Homma et al.
U.S. Appl. No. 14/240,214, filed Feb. 21, 2014, Homma et al.
U.S. Appl. No. 14/240,206, filed Feb. 21, 2014, Homma et al.
U.S. Appl. No. 14/240,248, filed Feb. 21, 2014, Homma et al.
International Search Report issued Jan. 8, 2013 in PCT/JP2012/076305.
Shigehiko Fukushima, "Shokuyoaburachu no Sterol no Teiryoho ni Tsuite", Bulletin of Osaka Prefectural Institute of Public Health Shokuhin Eisei Hen, vol. 10, 1979, pp. 47-52 with cover page.
Anna Johansson, et al., "The Content and Composition of Sterols and Sterol Esters in low Erucic Acid Rapeseed (*Brassica napus*)", Lipids, vol. 13, No. 10, 1978, pp. 658-665.
Ann M. Lees, et al., "Plant Sterols as Cholesterol-Lowering Agents: Clinical Trials in Patients with Hypercholesterolemia and Studies of Sterol Balance", Atherosclerosis, vol. 28, 1977, pp. 325-338.
Ikuo Ikeda, et al., "Serum Lipid", Lipid, vol. 5, No. 1, pp. 101-105.

* cited by examiner

*Primary Examiner* — Jared D Barsky
(74) *Attorney, Agent, or Firm* — Oblon, McClelland, Maier & Neustadt, L.L.P.

(57) ABSTRACT

Provided is a fat or oil composition, comprising the following components (A) and (B): (A) 0.4 to 6 mass % of a free type triterpene alcohol; and (B) 0.2 to 3 mass % of a free type phytosterol containing 20 mass % or more of β-sitosterol, in which a content mass ratio of the free type triterpene alcohol (A) to the free type phytosterol (B), [(A)/(B)], is 0.9 or more.

25 Claims, No Drawings

FAT COMPOSITION

FIELD OF THE INVENTION

The present invention relates to a fat or oil composition containing a phytosterol in a dissolved state.

BACKGROUND OF THE INVENTION

Phytosterols are steroid alcohols that widely exist in a variety of plants in a free state or in such a form as a fatty acid ester, a glycoside, or a ferulic acid ester. The phytosterols have excellent blood cholesterol-lowering actions, and hence the phytosterols have been blended in edible fats or oils. Among the phytosterols, β-sitosterol is considered to have an excellent cholesterol-lowering action (Non Patent Documents 1 and 2).

The phytosterols are hydrolyzed in the stages of extraction from natural products and condensation and purification of the extract, and mostly turn to phytosterols in a free state. There is a problem in that the phytosterols in a free state dissolve in edible fats or oils in only extremely small amounts.

Thus, studies have been made on developing a technology for solubilizing a phytosterol in an edible fat or oil. There are proposed, for example, a method involving solubilizing a phytosterol in an oil by using vitamin E and an emulsifier each in a large amount (Patent Document 1), and a method involving adding a phytosterol in the form of a fatty acid ester to a fat or oil (Patent Document 2), or the like. Further, it is reported that, when an edible fat or oil containing, together with a phytosterol, an oryzanol and a triterpene alcohol, which have similar physiological effects to those of the phytosterol, comprises a free type triterpene alcohol and a free type phytosterol each in a specified amount or less, the edible fat or oil is excellent (Patent Document 3).

CITATION LIST

Patent Document

[Patent Document 1] JP-A-10-179086
[Patent Document 2] JP-A-11-127779
[Patent Document 3] JP-A-2001-224309

Non Patent Document

[Non Patent Document 1] Atherosclerosis, 28, 325-338 (1977)
[Non Patent Document 2] The lipid vol. 5, No. 1, 101-105 (1994)

SUMMARY OF THE INVENTION

The present invention provides a fat or oil composition, comprising the following components (A) and (B):
 (A) 0.4 to 6 mass % of a free type triterpene alcohol; and
 (B) 0.2 to 3 mass % of a free type phytosterol containing 20 mass % or more of β-sitosterol,
 in which a content mass ratio of the free type triterpene alcohol (A) to the free type phytosterol (B), [(A)/(B)], is 0.9 or more.

DETAILED DESCRIPTION OF THE INVENTION

A conventional edible fat or oil in which a phytosterol is blended involved a problem in that, although its clear appearance is kept at the time of preparation, crystals of the phytosterol are formed when the edible fat or oil is stored, in particular, when it is stored under low temperature or under high-temperature and high-humidity conditions. An insoluble phytosterol is hardly absorbed in the body and hence it is difficult to allow its blood cholesterol-lowering action to be exhibited effectively.

Thus, the present invention relates to providing a fat or oil composition in which a phytosterol is dissolved at a high concentration and the crystallization of the phytosterol is suppressed even when the fat or oil composition is stored under low temperature or under high-temperature and high-humidity conditions.

The inventors of the present invention made intensive studies to solve the above-mentioned problems. As a result, the inventors found that a free type triterpene alcohol exhibits an excellent crystal suppression effect on a phytosterol and that, when a free type triterpene alcohol coexists within a specified range in a fat or oil, a fat or oil composition in which a free phytosterol, in particular, β-sitosterol is dissolved at a high concentration is obtained.

According to the present invention, it is possible to provide a fat or oil composition which has a high content of a phytosterol, in particular, β-sitosterol and is excellent in physiological effects, while the crystallization thereof is suppressed under low temperature or the like.

The term "triterpene alcohol" as used herein refers to a tetracyclic triterpene alcohol having 30 or 31 carbon atoms.

The triterpene alcohol can be obtained by, for example, extraction from rice, rice bran, a fat or oil containing the triterpene alcohol such as rice oil, or a fat or oil-processed product, or by hydrolysis of γ-oryzanol, or the like. Further, a commercially available product may be used.

In addition, the term "phytosterol" as used herein refers to a 4-desmethylsterol having 28 or 29 carbon atoms. The phytosterol and the triterpene alcohol are compounds clearly different from each other.

The phytosterol can be obtained by, for example: extraction from a plant such as a vegetable, pulses, or a cereal; hydrolysis of γ-oryzanol; or a known organic chemical synthesis method. In addition, a commercially available product may be used.

The triterpene alcohol and the phytosterol include a free type, a fatty acid ester type, and a ferulic acid ester type. The term "free type" as used herein refers to a compound having a hydroxyl group at the C-3 position of a steroid nucleus.

Examples of the free type triterpene alcohol (A) to be used in the present invention include cycloartenol, 24-methylenecycloartanol, cyclobranol, cycloartanol, cyclosadol, cycolaudenol, butyrospermol, and parkeol and the like. The free type triterpene alcohol can be used as a single compound or a mixture of the compounds. Of those, from the standpoint of physiological effects, one or two or more selected from cycloartenol, 24-methylenecycloartanol, and cyclobranol are preferably used, and cycloartenol, 24-methylenecycloartanol, or a combination thereof is more preferably used.

The free type triterpene alcohol can be measured in accordance with the method described in J. Am. Oil Chem. Soc., 82 (6), 439 (2005).

The fat or oil composition according to the present invention contains from 0.4 to 6 mass % (hereinafter simply referred to as "%") of the free type triterpene alcohol (A). By controlling the content of the component (A) within the predetermined range, the solubility of a free type phytosterol into a fat or oil can be enhanced, and hence the crystallization of the free type phytosterol can be suppressed when the fat or oil composition is stored, in particular, even when it is stored under low temperature. That is, the free type triterpene alcohol (A) can be used for improving the solubility, in a fat or oil, of a free type phytosterol containing 20% or more of β-sitosterol, and can be used for suppressing the crystallization of the free type phytosterol under normal temperature, low temperature, or high-temperature and high-humidity conditions. Further, the free type triterpene alcohol (A) can be used for improving the stability of a fat or oil containing from 0.2 to 3% of the free type phytosterol under normal temperature, low temperature, or high-temperature and high-humidity conditions.

The content of the free type triterpene alcohol (A) in the fat or oil composition is preferably 0.85% or more, more preferably 0.9% or more, more preferably 1.2% or more, more preferably 1.6% or more, even more preferably 2.1% or more from the standpoint of physiological effects, and is preferably 6% or less, more preferably 5% or less, more preferably from 0.4 to 5%, even more preferably from 0.4 to 4% from the standpoints of improving cool tolerance and improving stability under high-temperature and high-humidity conditions.

Further, the content of cycloartenol in the free type triterpene alcohol (A) is preferably from 15 to 100%, more preferably from 20 to 90%, even more preferably from 25 to 80%, from the standpoint of physiological effects.

The fat or oil composition according to the present invention contains from 0.2 to 3% of the free type phytosterol (B), and contains preferably from 0.2 to 2.5% thereof, more preferably from 0.2 to 2% thereof, from the standpoint of improving the storage stability.

The free type phytosterol (B) to be used in the present invention contains 20% or more of β-sitosterol. The content of β-sitosterol in the free type phytosterol is preferably from 20 to 100%, more preferably from 20 to 90%, more preferably from 20 to 80%, more preferably from 20 to 70%, more preferably from 20 to 60%, even more preferably from 20 to 40%, from the standpoint of improving the cool tolerance.

The free type phytosterol (B) preferably contains campesterol in addition to β-sitosterol from the standpoint of suppressing the crystallization thereof.

The content of the campesterol in the free type phytosterol (B) is preferably 5% or more, more preferably 10% or more, more preferably 20% or more, even more preferably 30% or more, is preferably 80% or less, more preferably 75% or less, even more preferably 70% or less, and specifically, is preferably from 5 to 80%, more preferably from 10 to 80%, more preferably from 20 to 75%, even more preferably from 30 to 70%, from the standpoint of improving stability under high-temperature and high-humidity conditions.

The free type phytosterol (B) may contain one or two or more selected from phytosterols other than β-sitosterol and campesterol such as α-sitosterol, stigmasterol, α-sitostanol, β-sitostanol, stigmastanol, campestanol, brassicasterol, fucosterol, isofucosterol, spinasterol, and avenasterol.

The free type phytosterol can be measured in accordance with the method described in J. Am. Oil Chem. Soc., 82(6), 439 (2005).

In the fat or oil composition according to the present invention, the content mass ratio of the free type triterpene alcohol (A) to the free type phytosterol (B), [(A)/(B)], is 0.9 or more, and is preferably from 0.9 to 6, more preferably from 0.9 to 5, more preferably from 0.9 to 4, more preferably from 0.9 to 3.5, even more preferably from 0.9 to 3, from the standpoints of enhancing the solubility of the free type phytosterol and suppressing the crystallization of the phytosterol.

In the fat or oil composition according to the present invention, the content of the fatty acid ester type triterpene alcohol is preferably less than 1.4%, more preferably less than 0.5%, more preferably less than 0.1%, more preferably less than 0.05%, even more preferably less than 0.01%, and is more preferably from 0 to 1.4%, more preferably from 0.0001 to 0.5%, more preferably from 0.0001 to 0.08%, even more preferably from 0.0001 to 0.04%, from the standpoint of improving the taste and flavor. The fatty acid ester type triterpene alcohol can be measured in accordance with the method described in J. Food Science, 65(8), 1395 (2000).

Further, the amount of the fatty acid ester type triterpene alcohol can be calculated on the basis of the amount of the total triterpene alcohols, the amount of the free type triterpene alcohol, and the amount of the ferulic acid ester type triterpene alcohol. The amount of the total triterpene alcohols can be measured in accordance with the method described in J. Am. Oil Chem. Soc., 82 (6), 439 (2005). The ferulic acid ester type triterpene alcohol can be measured in accordance with the method described in J. Food Science, 65(8), 1395 (2000) or Lipids, 30(3), 269 (1995).

Note that the term "fatty acid ester type triterpene alcohol" refers to a triterpene alcohol in which a fatty acid is bonded to the hydroxyl group, via an ester binding, at the C-3 position of a free type triterpene alcohol.

In addition, in the fat or oil composition according to the present invention, the content of γ-oryzanol is preferably less than 0.7%, more preferably less than 0.5%, more preferably less than 0.15%, more preferably less than 0.1%, more preferably less than 0.05%, more preferably less than 0.01%, more preferably less than 0.0034%, more preferably less than 0.001%, even more preferably less than 0.0002%, and is more preferably from 0 to 0.5%, more preferably from 0.000001 to 0.1%, more preferably from 0.000001 to 0.01%, more preferably from 0.000001 to 0.003%, even more preferably from 0.000001 to 0.0001%, from the standpoint of improving the taste and flavor. The term "γ-oryzanol" as used herein is a collective term for a ferulic acid 3-methoxy-4-hydroxycinnamic acid) ester of the triterpene alcohol or a sterol, and the γ-oryzanol is a substance present in rice oil, corn oil, or another cereal bran oil. The γ-oryzanol can be measured in accordance with the method described in J. Food Science, 65(8), 1395 (2000) or Lipids, 30(3), 269 (1995).

A fat or oil (edible fat or oil) that may be used in the fat or oil composition according to the present invention is not particularly limited, and examples thereof may include the following fats or oils: plant-derived fats or oils such as soybean oil, rapeseed oil, safflower oil, rice oil, corn oil, palm oil, sunflower oil, cotton seed oil, olive oil, sesame oil, peanut oil, Job's tears seed oil, wheat germ oil, Japanese basil oil, linseed oil, perilla oil, sacha inchi oil, walnut oil, kiwi seed oil, salvia seed oil, grape seed oil, macadamia nut oil, hazelnut oil, pumpkin seed oil, camellia oil, tea seed oil, borage oil, palm olein, palm stearin, coconut oil, palm kernel oil, cacao fat, sal fat, shea fat, and algae oil; animal-derived fats or oils such as fish oil, lard, beef tallow, and butter fat; or transesterified oils, hydrogenated oils, and fractionated oils thereof, or the like. The oils may each be used singly or may be mixed appropriately before use. Of those, from the standpoint of usability, a plant-derived fat or oil is preferably used, and a liquid fat or oil excellent in low-temperature resistance is more preferably used. The liquid fat or oil means a fat or oil that is in a liquid state at 20° C., when determined in accordance with a cold test described in Standard Methods for the Analysis of Fats, Oils and Related Materials 2.3.8-27. In addition, the edible fat or oil is preferably a refined fat or oil obtained by a refinement step.

In the fat or oil composition according to the present invention, the content of the fat or oil is preferably from 90 to 99.4%, more preferably from 94 to 99%, even more preferably from 97 to 99%, from the standpoint of the use thereof.

The fat or oil according to the present invention contains any one or more of a monoacylglycerol, a diacylglycerol, and a triacylglycerol. The content of the diacylglycerol in the fat or oil composition is preferably 19% or less, more preferably 9% or less, more preferably from 0.1 to 7%, even more preferably from 0.2 to 5%, from the standpoint of the industrial productivity of the fat or oil. Further, the content of the monoacylglycerol is preferably 3% or less, more preferably from 0 to 2%, from the standpoint of improving the taste and flavor. The content of the triacylglycerol is preferably 78% or more, more preferably 88% or more, more preferably 90% or more, even more preferably 92% or more, and is preferably 99.4% or less, more preferably 99% or less. Specifically, the content is preferably from 78 to 99.4%, more preferably from 88 to 99.4%, more preferably from 90 to 99.4%, even more preferably from 92 to 99%, from the standpoint of the industrial productivity of the fat or oil.

In addition, the content of a free fatty acid or a salt thereof comprised in the fat or oil composition according to the present invention is preferably 5% or less, more preferably from 0 to 2%, even more preferably from 0 to 1%, from the standpoints of the taste and flavor and the industrial productivity of the fat or oil.

The constituent fatty acids of the fat or oil in the fat or oil composition according to the present invention are not particularly limited and may be any of saturated fatty acids and unsaturated fatty acids. The ratio of the unsaturated fatty acids is preferably from 60 to 100%, more preferably from 70 to 100%, more preferably from 75 to 100%, even more preferably from 80 to 98%, from the standpoints of the appearance and industrial productivity of the fat or oil. The carbon numbers of the unsaturated fatty acids are preferably from 14 to 24, more preferably from 16 to 22, from the standpoint of the physiological effects.

In addition, the content of the saturated fatty acids in the constituent fatty acids of the fat or oil in the fat or oil composition is preferably 40% or less, more preferably from 0 to 30%, more preferably from 0 to 25%, even more preferably from 2 to 20%, from the standpoints of the appearance, the physiological effects, and the industrial productivity of the fat or oil. The carbon numbers of the saturated fatty acids are preferably from 14 to 24, more preferably from 16 to 22.

In addition, the content of an antioxidant in the fat or oil composition according to the present invention is preferably from 0.01 to 2%, more preferably from 0.01 to 1%, even more preferably from 0.01 to 0.5%, from the standpoint of oxidative stability at the time of each of preservation and cooking. The antioxidant includes preferably one or two or more selected from, for example, a natural antioxidant, tocopherol, ascorbyl palmitate, ascorbyl stearate, dibutylhydroxytoluene (BHT), and butylated hydroxyanisole (BHA), more preferably, for example, one or two or more selected from a natural antioxidant, tocopherol, and ascorbyl palmitate. Of those, ascorbyl palmitate and tocopherol are preferably used in combination.

The fat or oil composition according to the present invention can be used in the same manner as a general edible fat or oil, and can be widely applied to a variety of foods and beverages including the fat or oil.

In relation to the above-mentioned embodiment, the present invention discloses the following fat or oil compositions or uses.

<1> A fat or oil composition, comprising the following components (A) and (B):
  (A) 0.4 to 6 mass % of a free type triterpene alcohol; and
  (B) 0.2 to 3 mass of a free type phytosterol containing 20 mass % or more of β-sitosterol,
  in which a content mass ratio of the free type triterpene alcohol (A) to the free type phytosterol (B), [(A)/(B)], is 0.9 or more.
<2> The fat or oil composition according to the above-mentioned item <1>, in which the content of the free type triterpene alcohol (A) is preferably 0.85 mass % or more, more preferably 0.9 mass % or more, more preferably 1.2 mass % or more, more preferably 1.6 mass % or more, even more preferably 2.1 mass % or more.
<3> The fat or oil composition according to the above-mentioned item <1> or <2>, in which the content of the free type triterpene alcohol (A) is preferably 6 mass or less, more preferably 5 mass or less.
<4> The fat or oil composition according to the above-mentioned item <1>, in which the content of the free type triterpene alcohol (A) is preferably from 0.4 to 5 mass %, more preferably from 0.4 to 4 mass %.
<5> The fat or oil composition according to any one of the above-mentioned items <1> or <4>, in which the free type triterpene alcohol (A) comprises one or two or more selected from cycloartenol, 24-methylenecycloartanol, cyclobranol, cycloartanol, cyclosadol, cyclolaudenol, butyrospermol, and parkeol, preferably one or two or more selected from cycloartenol, 24-methylenecycloartanol, and cyclobranol, more preferably cycloartenol, 24-methylenecycloartanol, or a combination thereof.
<6> The fat or oil composition according to any one of the above-mentioned items <1> to <5>, in which the content of the free type phytosterol (B) is preferably from 0.2 to 2.5 mass %, more preferably from 0.2 to 2 mass %.
<7> The fat or oil composition according to any one of the above-mentioned items <1> to <6>, in which the content of β-sitosterol in the free type phytosterol (B) is preferably from 20 to 100 mass %, more preferably from 20 to 90 mass %, more preferably from 20 to 80 mass %, more preferably from 20 to 70 mass %, more preferably from 20 to 60 mass %, even more preferably from 20 to 40 mass %.
<8> The fat or oil composition according to any one of the above-mentioned items <1> to <7>, in which the free type phytosterol (B) contains campesterol in addition to β-sitosterol.
<9> The fat or oil composition according to the above-mentioned item <8>, in which the content of campesterol in the free type phytosterol (B) is 5 mass % or more, preferably 10 mass % or more, more preferably 20 mass % or more, even more preferably 30 mass % or more, is 80 mass % or less, preferably 75 mass % or less, more preferably 70 mass % or less, and is preferably from 5 to 80 mass %, more preferably from 10 to 80 mass %, more preferably from 20 to 75 mass %, even more preferably from 30 to 70 mass %.
<10> The fat or oil composition according to any one of the above-mentioned items <1> to <9>, in which a content mass ratio of the free type triterpene alcohol (A) to the free type phytosterol (B), [(A)/(B)], is preferably from 0.9 to 6, more preferably from 0.9 to 5, more preferably from 0.9 to 4, more preferably from 0.9 to 3.5, even more preferably from 0.9 to 3.
<11> The fat or oil composition according to any one of the above-mentioned items <1> to <10>, in which the content of a fat or oil is from 90 to 99.4 mass %, preferably from 94 to 99 mass %, more preferably from 97 to 99 mass %.

<12> The fat or oil composition according to any one of the above-mentioned items <1> to <11>, in which the content of a triacylglycerol is 78 mass % or more, preferably 88 mass % or more, more preferably 90 mass % or more, even more preferably 92 mass % or more, is 99.4 mass % or less, preferably 99 mass % or less, and is preferably from 78 to 99.4 mass %, more preferably from 88 to 99.4 mass %, more preferably from 90 to 99.4 mass %, even more preferably from 92 to 99 mass %.

<13> The fat or oil composition according to any one of the above-mentioned items <1> to <12>, in which constituent fatty acids of the fat or oil in the fat or oil composition comprise from 60 to 100 mass %, preferably from 70 to 100 mass %, more preferably from 75 to 100 mass %, even more preferably from 80 to 98 mass % of unsaturated fatty acids.

<14> The fat or oil composition according to any one of the above-mentioned items <1> to <13>, in which constituent fatty acids of the fat or oil in the fat or oil composition comprise 40 mass % or less, preferably from 0 to 30 mass %, more preferably from 0 to 25 mass %, even more preferably from 2 to 20 mass % of saturated fatty acids.

<15> The fat or oil composition according to any one of the above-mentioned items <1> to <14>, in which the content of a fatty acid ester type triterpene alcohol is less than 1.4 mass %, preferably less than 0.5 mass %, more preferably less than 0.1 mass %, more preferably less than 0.05 mass %, even more preferably less than 0.01 mass %.

<16> The fat or oil composition according to any one of the above-mentioned items <1> to <14>, in which the content of a fatty acid ester type triterpene alcohol is from 0 to 1.4 mass %, preferably from 0.0001 to 0.5 mass %, more preferably from 0.0001 to 0.08 mass %, even more preferably from 0.0001 to 0.04 mass %.

<17> The fat or oil composition according to any one of the above-mentioned items <1> to <16>, in which the content of γ-oryzanol is less than 0.7 mass %, preferably less than 0.5 mass %, more preferably less than 0.15 mass %, more preferably less than 0.1 mass %, more preferably less than 0.05 mass %, more preferably less than 0.01 mass %, more preferably less than 0.0034 mass %, more preferably less than 0.001 mass %, even more preferably less than 0.0002 mass %.

<18> The fat or oil composition according to any one of the above-mentioned items <1> to <16>, in which the content of γ-oryzanol is from 0 to 0.5 mass %, preferably from 0.000001 to 0.1 mass %, more preferably from 0.000001 to 0.01 mass %, more preferably from 0.000001 to 0.003 mass %, even more preferably from 0.000001 to 0.0001 mass %. <19> The fat or oil composition according to any one of the above-mentioned items <1> to <18>, further comprising from 0.01 to 2 mass %, preferably from 0.01 to 1 mass %, more preferably from 0.01 to 0.5 mass % of an antioxidant.

<20> The fat or oil composition according to the above-mentioned item <19>, in which the antioxidant comprises one or two or more selected from a natural antioxidant, tocopherol, ascorbylpalmitate, ascorbyl stearate, dibutylhydroxytoluene, and butylated hydroxyanisole, preferably one or two or more selected from tocopherol, ascorbyl palmitate, and ascorbyl stearate, more preferably a combination of tocopherol and ascorbyl palmitate.

<21> Use of the fat or oil composition according to any one of the above-mentioned items <1> to <20> as an edible fat or oil.

<22> Use of a free type triterpene alcohol for improving a solubility, in a fat or oil, of a free type phytosterol containing 20 mass % or more of β-sitosterol.

<23> Use of a free type triterpene alcohol for suppressing a crystallization of a free type phytosterol containing 20 mass % or more of β-sitosterol, in a fat or oil under normal temperature, low temperature, or high-temperature and high-humidity conditions.

<24> Use of a free type triterpene alcohol for improving a stability of a fat or oil which contains from 0.2 to 3 mass of a free type phytosterol containing 20 mass or more of β-sitosterol, under normal temperature, low temperature, or high-temperature and high-humidity conditions.

<25> The use according to any one of the above-mentioned items <22> to <24>, in which the content of β-sitosterol in the free type phytosterol is preferably from 20 to 100 mass %, more preferably from 20 to 90 mass %, more preferably from 20 to 80 mass %, more preferably from 20 to 70 mass %, more preferably from 20 to 60 mass %, even more preferably from 20 to 40 mass %.

<26> The use according to anyone of the above-mentioned items <22> to <25>, in which the free type phytosterol contains campesterol in addition to β-sitosterol.

<27> The use according to the above-mentioned item <26>, in which the content of campesterol in the free type phytosterol is 5 mass or more, preferably 10 mass % or more, more preferably 20 mass % or more, even more preferably 30 mass or more, is 80 mass or less, preferably 75 mass or less, more preferably 70 mass % or less, and is preferably from 5 to 80 mass %, more preferably from 10 to 80 mass %, more preferably from 20 to 75 mass %, even more preferably from 30 to 75 mass %.

<28> The use according to any one of the above-mentioned items <22> to <27>, in which the free type triterpene alcohol comprises one or two or more selected from cycloartenol, 24-methylenecycloartanol, cyclobranol, cycloartanol, cyclosadol, cyclolaudenol, butyrospermol, and parkeol, preferably one or two or more selected from cycloartenol, 24-methylenecycloartanol, and cyclobranol, more preferably cycloartenol, 24-methylenecycloartanol, or a combination thereof.

<29> The use according to any one of the above-mentioned items <22> to <28>, in which the content of the free type phytosterol in the fat or oil is preferably from 0.2 to 2.5 mass %, more preferably from 0.2 to 2 mass %.

<30> The use according to any one of the above-mentioned items <22> to <29>, in which the free type triterpene alcohol is comprised in the fat or oil, so that the content of the free type triterpene alcohol is 0.4 mass % or more, preferably 0.85 mass % or more, more preferably 0.9 mass % or more, more preferably 1.2 mass % or more, more preferably 1.6 mass or more, even more preferably 2.1 mass or more.

<31> The use according to any one of the above-mentioned items <22> to <30>, in which the free type triterpene alcohol is comprised in the fat or oil, so that the content of the free type triterpene alcohol is 6 mass % or less, preferably 5 mass % or less.

<32> The use according to any one of the above-mentioned items <22> to <29>, in which the free type triterpene alcohol is comprised in the fat or oil, so that the content of the free type triterpene alcohol is from 0.4 to 6 mass %, preferably from 0.4 to 5 mass, more preferably from 0.4 to 4 mass %.

<33> The use according to any one of the above-mentioned items <22> to <32>, in which the free type triterpene alcohol and the free type phytosterol are comprised in the fat or oil, so that the content mass ratio between the free type triterpene alcohol and the free type phytosterol, [(A)/(B)], is 0.9 or more, preferably from 0.9 to 6, more preferably from 0.9 to 5, more preferably from 0.9 to 4, more preferably from 0.9 to 3.5, even more preferably from 0.9 to 3.

EXAMPLES (Analysis Methods)
(i) Composition of Glycerides in Fat or Oil

About 10 mg of a fat or oil sample and 0.5 mL of a trimethylsilylating agent ("Silylating agent TH," manufactured by Kanto Chemical Co., Inc.) were placed in a glass sample bottle, and the bottle was sealed and heated at 70° C. for 15 minutes. 1.0 mL of water and 1.5 mL of hexane were added thereto, and the bottle was shaken. The bottle was allowed to stand still, and then the upper layer was analyzed by gas-liquid chromatography (GLC).

<GLC Analysis Conditions>
(Conditions)
Apparatus: Agilent 6890 Series (manufactured by Agilent Technologies)
Integrator: ChemStation B.02.01 SR2 (manufactured by Agilent Technologies)
Column: DB-1ht (manufactured by Agilent J&W)
Carrier gas: 1.0 mL He/min
Injector: Split (1:50), T=340° C.
Detector: FID, T=350° C.
Oven temperature: The temperature was raised from 80° C. at 10° C./min to 340° C., and kept for 15 minutes.

(ii) Composition of Constituent Fatty Acids of Fat or Oil

Fatty acid methyl esters were prepared in accordance with "Preparation method for fatty acid methyl ester (2.4.1.-1996)" described in "Standard Methods for the Analysis of Fats, Oils and Related Materials" edited by Japan Oil Chemists' Society, and the resultant fat or oil samples were subjected to measurement in accordance with American Oil Chemists. Society Official Method Ce 1f-96 (GLC method).

<GLC Analysis Conditions>
Column: CP-SIL88 100 m×0.25 mm×0.2 μm (VARIAN)
Carrier gas: 1.0 mL He/min
Injector: Split (1:200), T=250° C.
Detector: FID, T=250° C.
Oven temperature: The temperature was kept at 174° C. for 50 minutes, raised to 220° C. at 5° C./min, and kept for 25 minutes.

(iii) Free Type Triterpene Alcohol and Free Type Phytosterol

Samples were prepared in accordance with J. Am. Oil Chem. Soc., (6), 439 (2005), and were subjected to measurement by GLC. Specifically, the measurement was performed by the following method.

About 500 mg of a fat or oil sample was dissolved in about 5 mL of hexane, and the solution was charged into an SPE cartridge (Sep-Pak Silica, 5 g, GL Sciences Inc.). Washing was performed with about 40 mL of hexane/ether (95/5 in volume ratio), followed by elution with about 40 mL of ethanol/ether/hexane (50/25/25 in volume ratio), and an ethanol/ether/hexane-eluted fraction was separated. The solvent was distilled off from the fraction obtained, and the residue was charged into PTLC (Si 60, 20×20×00.1 cm, Merck KGaA). Development was performed with hexane/ether/acetic acid (90/10/2 in volume ratio) and chloroform/ether (95/5 in volume ratio) in the stated order, and then a free type triterpene alcohol fraction and a free type phytosterol fraction were separated. 0.5 mL of a trimethylsilylating agent ("Silylating agent TH," manufactured by Kanto Chemical Co., Inc.) was added to the free type triterpene alcohol fraction or free type phytosterol fraction separated in a container. The container was sealed and heated at 70° C. for 30 minutes. 1.0 mL of water and 1.5 mL of hexane were added thereto, followed by shaking. The container was allowed to stand still, and then the upper layer was analyzed by gas-liquid chromatography (GLC), thereby measuring the amount of the free type triterpene alcohol and the amount of the free type phytosterol (mass %).

<GLC Analysis Conditions>
Column: DB-1ht 10.0 m×0.25 mm×0.10 μm (Agilent)
Carrier gas: 1.0 mL He/min
Injector: Split (1:80), T=340° C.
Detector: FID, T=350° C.
Oven temperature: The temperature was raised from 200° C. at 10° C./min to 340° C., and kept for 10 minutes.

(iv) Total Triterpene Alcohols

Samples were prepared in accordance with J. Am. Oil Chem. Soc., (6), 439 (2005), and were subjected to measurement by GLC. Specifically, the measurement was performed by the following method.

About 5 g of a fat or oil sample and about 20 mL of a 2 N potassium hydroxide/ethanol solution were added into a conical flask, followed by heating at 80° C. for 60 minutes. After the mixture was cooled to room temperature, an internal standard (cholesterol), 15 mL of water, and 10 mL of hexane were added, followed by shaking. After the mixture was allowed to stand still, the upper layer was separated and was concentrated. 0.5 mL of a trimethylsilylating agent ("Silylating agent TH," manufactured by Kanto Chemical Co., Inc.) was added to the concentrate in a container, and the container was sealed and heated at 70° C. for 30 minutes. 1.0 mL of water and 1.5 mL of hexane were added thereto, followed by shaking. The container was allowed to stand still, and then the upper layer was analyzed by gas-liquid chromatography (GLC), thereby measuring the amount of the total triterpene alcohols (mass %). The same GLC analysis conditions as those in (iii) were used.

(v) γ-Oryzanol

Samples were prepared in accordance with Lipids, 30 (3), 269 (1995), and the resultant samples were subjected to measurement by HPLC-UV. Specifically, the measurement was performed by the following method.

About 100 mg of a fat or oil sample were dissolved in ethyl acetate to obtain a solution (10 mL), and the solution was analyzed by an HPLC method.

<HPLC Analysis Conditions>
Column: Inertsil ODS-3, 4.6 mm×250 mm, 5 μm (GL Sciences Inc.)
Column temperature: 40° C.
Flow rate: 1.2 mL/min
Detection: UV 325 nm
Eluent: acetonitrile/butanol/acetic acid (volume ratio: 82/3/2)

(vi) Fatty Acid Ester Type Triterpene Alcohol

The amount of the free type triterpene alcohol and the amount of γ-oryzanol which was converted to the free type were subtracted from the amount of the total triterpene alcohols, thereby calculating the amount of a fatty acid ester type triterpene alcohol which was converted to the free type. Conversion from the free type to the fatty acid ester type was performed, yielding the amount (mass %) of a fatty acid ester type triterpene alcohol. Note that, when the conversion from the free type to the fatty acid ester type was performed, calculation was made on the assumption that the linked fatty acid was oleic acid.

(Free Type Triterpene Alcohol and Free Type Phytosterol)

The free type triterpene alcohol was prepared by hydrolyzing a commercially available oryzanol (Wako Pure Chemical Industries, Ltd.) and separating and purifying the reaction product by silica-gel column chromatography. The composition of the preparation was as follows: cycloartenol: 40%, 24-methylenecycloartanol: 60%.

There was used, as the free type phytosterol (4-desmethylsterol), a preparation obtained by hydrolyzing a commercially available oryzanol (Wako Pure Chemical Industries, Ltd.) and separating and purifying the reaction product by silica-gel column chromatography, a commercially available phytosterol formulation (ADM Japan Ltd.), or β-sitosterol or campesterol as a reagent (both manufactured by Tama Biochemical Co., Ltd., purity: 99%). The composition of the preparation obtained from the oryzanol was as follows: campesterol: 62%, β-sitosterol: 31%, stigmasterol: 6%. The composition of the phytosterol formulation (ADM Japan Ltd.) was as follows: campesterol: 26%, β-sitosterol: 51%, stigmasterol: 210%.

(Raw Material Fat or Oil)

The composition of glycerides and the composition of fatty acids in refined rapeseed oil were as shown in Table 1. Further, the content of each of free type and fatty acid ester type triterpene alcohols and the content of γ-oryzanol were 0% in the refined rapeseed oil.

TABLE 1

|  | Refined rapeseed oil |
|---|---|
| Composition of glycerides (mass %) | |
| MAG | 0.0 |
| DAG | 0.9 |
| TAG | 99.1 |
| Composition of fatty acids (mass %) | |
| C14:0 | 0.0 |
| C16:0 | 4.3 |
| C16:1 | 0.2 |
| C18:0 | 2.0 |
| C18:1 | 60.5 |
| C18:2 | 21.0 |
| C18:3 | 10.8 |
| C20:0 | 0.6 |
| C20:1 | 0.4 |
| C22:0 | 0.0 |
| C24:0 | 0.1 |

MAG: Monoacylglycerol
DAG: Diacylglycerol
TAG: Triacylglycerol (Preparation of Fat or Oil Composition)

Examples 1 to 14 and Comparative Examples 1 to 9

The free type triterpene alcohol, the β-sitosterol as a reagent, and the campesterol as a reagent were blended at a ratio shown in Table 2 into the refined rapeseed oil (manufactured by The Nisshin OilliO Group, Ltd.), respectively. Each mixture was mixed and dissolved by using a stirrer while its temperature was kept at 50° C. until the mixture turned entirely clear, thus preparing each fat or oil composition. Table 2 shows the content of each of the free type triterpene alcohol, the free type phytosterol, β-sitosterol, and campesterol in each fat or oil composition.

Examples 15 to 27 and Comparative Examples 10 to 17

The free type triterpene alcohol, the preparation obtained from oryzanol (Examples 15 to 24 and Comparative Examples 10 to 17), and the commercially available phytosterol formulation (Examples 25 to 27) were blended at a ratio shown in Table 3 into the refined rapeseed oil (manufactured by The Nisshin OilliO Group, Ltd.), respectively. Each mixture was mixed and dissolved by using a stirrer while its temperature was kept at 50° C. until the mixture turned entirely clear, thus preparing each fat or oil composition. Table 3 shows the content of each of the free type triterpene alcohol, free type phytosterol, β-sitosterol, and campesterol in each fat or oil composition.

Note that the content of a fatty acid ester type triterpene alcohol and the content of γ-oryzanol were 0% in each fat or oil composition.

20 g of each fat or oil composition prepared as mentioned above were fed into a 30 mL-vial, and were allowed to stand still. The storage stability thereof was evaluated visually as follows.

(Evaluation of Storage Stability at 25° C.)

Nine panelists evaluated the appearance of a fat or oil composition stored at 25° C. for one week in accordance with the following evaluation criteria, and an average value of their scores was calculated as a score of the storage stability. Tables 2 and 3 show the results.

(Storage Stability)

4: The appearance is good.

3: The appearance is generally good but barely foggy.

2: The appearance is slightly inferior and slightly foggy.

1: The appearance is inferior and cloudy.

(Evaluation of Cool Tolerance)

Nine panelists evaluated the appearance of a fat or oil composition stored at 0° C. for one week in accordance with the following evaluation criteria, and an average value of their scores was calculated as a score of the cool tolerance. Tables 2 and 3 show the results.

(Cool Tolerance)

4: The appearance is good.

3: The appearance is generally good but barely foggy.

2: The appearance is slightly inferior and slightly foggy.

1: The appearance is inferior and cloudy.

(Evaluation of Storage Stability Under High-temperature and High-humidity Conditions)

Nine panelists evaluated the appearance of a fat or oil composition stored at a humidity of 80% and 40° C. for one week in accordance with the following evaluation criteria, and an average value of their scores was calculated as a score of the storage stability. Tables 2 and 3 show the results.

(Storage Stability Under High-temperature and High-humidity Conditions)

4: The appearance is good.

3: The appearance is generally good but crystals are precipitated in a slight amount on a liquid surface.

2: The appearance is slightly inferior and crystals are precipitated on a liquid surface.

1: The appearance is inferior and cloudy with crystals precipitated over the entirety.

TABLE 2

| (mass %) | | Example | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| Blend | Free type triterpene alcohol (A) | 0.50 | 0.90 | 1.20 | 0.50 | 1.30 | 2.00 | 4.00 | 1.30 | 2.00 | 4.00 | 2.00 | 4.00 | 5.00 | 5.00 |
| | Free type phytosterol (B) | 0.50 | 0.50 | 0.50 | 0.50 | 1.10 | 1.10 | 1.10 | 1.10 | 2.00 | 2.00 | 2.00 | 2.00 | 2.00 | 2.50 |
| | β-Sitosterol | 0.50 | 0.50 | 0.50 | 0.20 | 1.10 | 1.10 | 1.10 | 0.50 | 2.00 | 2.00 | 1.00 | 1.00 | 1.00 | 1.00 |
| | Campesterol | 0.00 | 0.00 | 0.00 | 0.30 | 0.00 | 0.00 | 0.00 | 0.60 | 0.00 | 0.00 | 1.00 | 1.00 | 1.00 | 1.50 |
| | (β-sitosterol)/(free type phytosterol) | 1.00 | 1.00 | 1.00 | 0.40 | 1.00 | 1.00 | 1.00 | 0.45 | 1.00 | 1.00 | 0.50 | 0.50 | 0.50 | 0.40 |
| | (campesterol/(free type phytosterol) | 0.00 | 0.00 | 0.00 | 0.60 | 0.00 | 0.00 | 0.00 | 0.55 | 0.00 | 0.00 | 0.50 | 0.50 | 0.50 | 0.60 |
| | (A)/(B) | 1.0 | 1.8 | 2.4 | 1.0 | 1.2 | 1.8 | 3.6 | 1.2 | 1.0 | 2.0 | 1.0 | 2.0 | 2.5 | 2.0 |
| Evaluation | Storage stability (at 25° C. for one week) | 4 | 4 | 4 | 4 | 4 | 4 | 4 | 4 | 4 | 4 | 4 | 4 | 4 | 4 |
| | Cool tolerance (at 0° C. for one week) | 3 | 3 | 3 | 4 | 3 | 3 | 3 | 4 | 3 | 3 | 4 | 4 | 4 | 4 |
| | Stability under high-temperature and high-humidity conditions (at 40° C. and 80% humidity for one week) | 4 | 4 | 4 | 4 | 4 | 4 | 3 | 4 | 4 | 4 | 4 | 4 | 4 | 4 |

| (mass %) | | Comparative Example | | | | | | | | |
|---|---|---|---|---|---|---|---|---|---|---|
| | | 1 | 2 | 3 | 4 | 5 | 6 | 7 | 8 | 9 |
| Blend | Free type triterpene alcohol (A) | 0.00 | 0.00 | 0.00 | 0.20 | 0.20 | 0.30 | 0.00 | 0.00 | 1.30 |
| | Free type phytosterol (B) | 0.50 | 0.50 | 0.50 | 1.10 | 1.10 | 1.00 | 2.00 | 2.00 | 1.30 |
| | β-Sitosterol | 0.50 | 0.20 | 0.30 | 1.10 | 0.50 | 0.00 | 2.00 | 1.00 | 0.00 |
| | Campesterol | 0.00 | 0.30 | 0.20 | 0.00 | 0.60 | 1.00 | 0.00 | 1.00 | 1.30 |
| | (β-sitosterol)/(free type phytosterol) | 1.00 | 0.40 | 0.60 | 1.00 | 0.45 | 0.00 | 1.00 | 0.50 | 0.00 |
| | (campesterol/(free type phytosterol) | 0.00 | 0.60 | 0.40 | 0.00 | 0.55 | 1.00 | 0.00 | 0.50 | 1.00 |
| | (A)/(B) | 0.0 | 0.0 | 0.0 | 0.2 | 0.2 | 0.3 | 0.0 | 0 | 1.0 |
| Evaluation | Storage stability (at 25° C. for one week) | 4 | 4 | 4 | 3 | 3 | 3 | 2 | 2 | 4 |
| | Cool tolerance (at 0° C. for one week) | 3 | 4 | 4 | 3 | 4 | 2 | 3 | 4 | 3 |
| | Stability under high-temperature and high-humidity conditions (at 40° C. and 80% humidity for one week) | 1 | 1 | 1 | 1 | 1 | 1 | 1 | 1 | 1 |

TABLE 3

| (mass %) | | Example | | | | | | | | | | | | |
|---|---|---|---|---|---|---|---|---|---|---|---|---|---|---|
| | | 15 | 16 | 17 | 18 | 19 | 20 | 21 | 22 | 23 | 24 | 25 | 26 | 27 |
| Blend | Free type triterpene alcohol (A) | 0.40 | 1.00 | 0.50 | 1.00 | 1.00 | 2.00 | 2.00 | 4.00 | 3.00 | 6.00 | 2.50 | 3.00 | 6.00 |
| | Free type phytosterol (B) | 0.20 | 0.20 | 0.50 | 0.50 | 1.00 | 1.00 | 2.00 | 2.00 | 3.00 | 3.00 | 2.43 | 2.43 | 2.43 |
| | β-Sitosterol | 0.06 | 0.06 | 0.16 | 0.16 | 0.31 | 0.31 | 0.63 | 0.63 | 0.94 | 0.94 | 1.26 | 1.26 | 1.26 |
| | Campesterol | 0.12 | 0.12 | 0.31 | 0.31 | 0.62 | 0.62 | 1.25 | 1.25 | 1.87 | 1.87 | 0.66 | 0.66 | 0.66 |
| | (β-sitosterol)/(free type phytosterol) | 0.31 | 0.31 | 0.31 | 0.31 | 0.31 | 0.31 | 0.31 | 0.31 | 0.31 | 0.31 | 0.52 | 0.52 | 0.52 |
| | (campesterol/(free type phytosterol) | 0.62 | 0.62 | 0.62 | 0.62 | 0.62 | 0.62 | 0.62 | 0.62 | 0.62 | 0.62 | 0.27 | 0.27 | 0.27 |
| | (A)/(B) | 2.0 | 5.0 | 1.0 | 2.0 | 1.0 | 2.0 | 1.0 | 2.0 | 1.0 | 2.0 | 1.0 | 1.2 | 2.5 |
| Evaluation | Storage stability (at 25° C. for one week) | 4 | 4 | 4 | 4 | 4 | 4 | 4 | 4 | 2 | 2 | 3 | 3 | 3 |
| | Cool tolerance (at 0° C. for one week) | 4 | 4 | 4 | 4 | 4 | 4 | 4 | 4 | 4 | 4 | 4 | 4 | 4 |
| | Stability under high-temperature and high-humidity conditions (at 40° C. and 80% humidity for one week) | 4 | 4 | 4 | 4 | 4 | 4 | 4 | 4 | 3 | 2 | 4 | 4 | 2 |

TABLE 3-continued

|  |  | Comparative Example | | | | | | | |
| --- | --- | --- | --- | --- | --- | --- | --- | --- | --- |
|  | (mass %) | 10 | 11 | 12 | 13 | 14 | 15 | 16 | 17 |
| Blend | Free type triterpene alcohol (A) | 0.00 | 0.00 | 0.00 | 0.00 | 4.00 | 0.50 | 7.00 | 7.00 |
|  | Free type phytosterol (B) | 0.50 | 1.00 | 2.00 | 3.00 | 4.00 | 4.00 | 1.00 | 3.00 |
|  | β-Sitosterol | 0.16 | 0.31 | 0.63 | 0.94 | 1.25 | 1.25 | 0.31 | 0.94 |
|  | Campesterol | 0.31 | 0.62 | 1.25 | 1.87 | 2.49 | 2.49 | 0.62 | 1.87 |
|  | (β-sitosterol)/(free type phytosterol) | 0.31 | 0.31 | 0.31 | 0.31 | 0.31 | 0.31 | 0.31 | 0.31 |
|  | (campesterol)/(free type phytosterol) | 0.62 | 0.62 | 0.62 | 0.62 | 0.62 | 0.62 | 0.62 | 0.62 |
|  | (A)/(B) | 0.0 | 0.0 | 0.0 | 0.0 | 1.0 | 0.1 | 7.0 | 2.3 |
| Evaluation | Storage stability (at 25° C. for one week) | 4 | 3 | 2 | 1 | 3 | 2 | 2 | 2 |
|  | Cool tolerance (at 0° C. for one week) | 2 | 2 | 1 | 1 | 1 | 1 | 1 | 1 |
|  | Stability under high-temperature and high-humidity conditions (at 40° C. and 80% humidity for one week) | 1 | 1 | 1 | 1 | 2 | 1 | 2 | 1 |

As shown in Tables 2 and 3, it was confirmed that the fat or oil compositions according to the present invention were excellent in storage stability, in particular, cool tolerance and storage stability under high-temperature and high-humidity conditions, in comparison to those of Comparative Examples.

The invention claimed is:

1. A fat or oil composition, comprising components (A) and (B) mixed and dissolved in a fat or oil:
   (A) 0.4 to 6 mass % of a free type triterpene alcohol; and
   (B) 0.2 to 3 mass % of a free type phytosterol comprising 20 mass % or more of β-sitosterol,
   wherein a content mass ratio of the free type triterpene alcohol (A) to the free type phytosterol (B), [(A)/(B)], is 0.9 or more, and
   wherein the free type triterpene alcohol and the free type phytosterol are maintained in the composition in a non-esterified state.

2. The fat or oil composition according to claim 1, wherein the content of the free type triterpene alcohol (A) is from 0.4 to 5%.

3. The fat or oil composition according to claim 1, wherein the content of the free type triterpene alcohol (A) is from 0.4 to 4%.

4. The fat or oil composition according to claim 1, wherein the content of the free type phytosterol (B) is from 0.2 to 2.5 mass %.

5. The fat or oil composition according to according to claim 1, wherein the content of the free type phytosterol (B) is from 0.2 to 2 mass %.

6. The fat or oil composition according to claim 1, wherein the content mass ratio of the free type triterpene alcohol (A) to the free type phytosterol (B), [(A)/(B)], is from 0.9 to 6.

7. The fat or oil composition according to claim 1, wherein the content mass ratio of the free type triterpene alcohol (A) to the free type phytosterol (B), [(A)/(B)], is from 0.9 to 3.5.

8. The fat or oil composition according to claim 1, wherein the content mass ratio of the free type triterpene alcohol (A) to the free type phytosterol (B), [(A)/(B)], is from 0.9 to 3.

9. The fat or oil composition according to claim 1, wherein the content of β-sitosterol in the free type phytosterol (B) is from 20 to 70 mass %.

10. The fat or oil composition according to claim 1, wherein the content of β-sitosterol in the free type phytosterol (B) is from 20 to 40 mass %.

11. The fat or oil composition according to claim 1, further comprising from 78 to 99.4 mass % of a triacylglycerol.

12. The fat or oil composition according to claim 1, wherein the free type phytosterol (B) further comprises campesterol.

13. The fat or oil composition according to claim 12, wherein a content of the campesterol in the free type phytosterol (B) is from 5 to 80%.

14. The fat or oil composition according to claim 1, wherein the free type triterpene alcohol as the component (A) comprises at least one selected from the group consisting of cycloartenol, 24-methylenecycloartanol, and cyclobranol.

15. The fat or oil composition according to claim 1, further comprising greater than 0 mass % and less than 0.7 mass % of γ-oryzanol.

16. The fat or oil composition according to claim 15, comprising greater than 0 mass % and less than 0.0034 mass % of the γ-oryzanol.

17. The fat or oil composition according to claim 1, further comprising a fatty acid ester type triterpene alcohol, which is present in an amount of greater than 0 mass % and less than 1.4 mass %, wherein said fatty acid ester type triterpene alcohol is not an esterified product of (A).

18. The fat or oil composition according to claim 1, further comprising a fatty acid ester type triterpene alcohol, which is present in an amount of greater than 0 mass % and less than 0.05 mass %, wherein said fatty acid ester type triterpene alcohol is not an esterified product of (A).

19. The fat or oil composition according to claim 1, wherein constituent fatty acids of the fat or oil in the fat or oil composition comprise from 60 to 100 mass % of unsaturated fatty acids.

20. The fat or oil composition according to claim 1, wherein constituent fatty acids of the fat or oil in the fat or oil composition comprise 40 mass % or less of saturated fatty acids.

21. The fat or oil composition according to claim 1, wherein a content of the free type triterpene alcohol (A) is from 0.85 to 6 mass %.

22. The fat or oil composition according to claim 1, wherein a content of the free type triterpene alcohol (A) is from 0.9 to 6 mass %.

23. The fat or oil composition according to claim 1, wherein a content of the free type triterpene alcohol (A) is from 1.2 to 6 mass %.

24. The fat or oil composition according to claim 1, wherein a content of the free type triterpene alcohol (A) is from 1.6 to 6 mass %.

25. The fat or oil composition according to claim 1, wherein a content of the free type triterpene alcohol (A) is from 2.1 to 6 mass %.

* * * * *